United States Patent [19]

Schmidt et al.

[11] 4,251,092

[45] Feb. 17, 1981

[54] PRESSURE SENSITIVE CARBONLESS DUPLICATING SYSTEMS AND THERMAL MARKING SYSTEMS

[75] Inventors: Paul J. Schmidt, Sharonville; William M. Hung, Cincinnati, both of Ohio

[73] Assignee: Sterling Drug Inc., New York, N.Y.

[21] Appl. No.: 963,955

[22] Filed: Nov. 27, 1978

Related U.S. Application Data

[63] Continuation-in-part of Ser. No. 821,926, Aug. 4, 1977, Pat. No. 4,182,714, which is a continuation-in-part of Ser. No. 755,376, Dec. 29, 1976, abandoned.

[51] Int. Cl.³ ............................................... B41L 1/20
[52] U.S. Cl. ................................. 282/27.5; 427/150; 427/151; 427/152; 428/306; 428/914
[58] Field of Search ..................... 427/150, 151, 152; 282/27.5; 428/914, 306

[56] References Cited

U.S. PATENT DOCUMENTS

| | | | |
|---|---|---|---|
| 4,075,224 | 2/1978 | Crounse | 427/151 |
| 4,104,437 | 8/1978 | Vincent | 427/151 |
| 4,151,748 | 5/1979 | Baum | 427/151 |

*Primary Examiner*—Ronald H. Smith
*Assistant Examiner*—Janyce A. Bell
*Attorney, Agent, or Firm*—Paul E. Dupont; B. Woodrow Wyatt

[57] ABSTRACT

3-Heteroaryl-3-(diphenylamino)phthalides useful as color formers in pressure-sensitive carbonless duplicating systems, thermal marking systems and hectographic copying systems are prepared by reacting 2-(heteroarylcarbonyl)benzoic acids with diphenylamines.

13 Claims, No Drawings

PRESSURE SENSITIVE CARBONLESS DUPLICATING SYSTEMS AND THERMAL MARKING SYSTEMS

CROSS-REFERENCE TO RELATED APPLICATIONS

This application is a continuation-in-part of copending application Ser. No. 821,926, filed Aug. 4, 1977, now U.S. Pat. No. 4,182,714, patented Jan. 8, 1980, in turn a continuation-in-part of application Ser. No. 755,376 filed Dec. 29, 1976, now abandoned.

BACKGROUND OF THE INVENTION

1. Field of the Invention

This invention relates to a group of compounds classified in the field of organic chemistry as 3-heteroaryl-3-(diphenylamino)phthalides useful as color formers in pressure-sensitive carbonless duplicating systems, thermal marking systems and hectographic or spirit-reproducing copying systems; to processes for the preparation thereof; and to pressure-sensitive duplicating systems, thermal marking systems and hectographic copying systems containing the same.

2. Description of the Prior Art

Several classes of organic compounds of widely diverse structural types are known to be useful as color formers for carbonless duplicating systems. Among the more widely recognized classes, there may be named phenothiazines, for example, 2'-anilino-6'-diethylaminofluoran; phthalides, the class with which this invention is concerned, for example, crystal violet lactone; and various other types of color formers currently employed in commercially accepted carbonless duplicating systems. Typical of the many such systems taught in the prior art are those described in U.S. Pat. Nos. 2,712,507, 2,800,457 and 3,041,289 which issued July 5, 1955, July 23, 1957 and June 26, 1962, respectively. Many of the color formers in the prior art suffer one or more disadvantages such as low tinctorial strength, poor light stability, low resistance to sublimation and low solubility in common organic solvents, the latter disadvantage thus requiring the use of specialized and expensive solvents in order to obtain microencapsulated solutions of sufficient concentration for use in pressure-sensitive copying systems.

The following appear to constitute the most relevant prior art relative to the present invention.

U.S. Pat. No. 3,736,168, issued May 29, 1973 discloses in most pertinent part a series of phthalides stated to be useful as color formers in pressure-sensitive copying paper and having the formula:

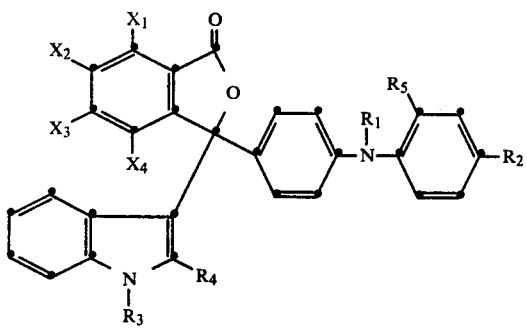

wherein inter alia $X_1$ and $X_4$ are hydrogen or chloro; $X_2$ and $X_3$ are hydrogen, chloro, dimethylamino or diethylamino; $R_1$ and $R_3$ are hydrogen, methyl or ethyl; $R_2$ is hydrogen, methyl or ethoxy; $R_4$ is methyl, ethyl or phenyl; and $R_5$ is hydrogen or methyl.

U.S. Pat. No. 3,491,112, issued Jan. 20, 1970 discloses the following phthalides which are stated to be useful in pressure-sensitive record materials:

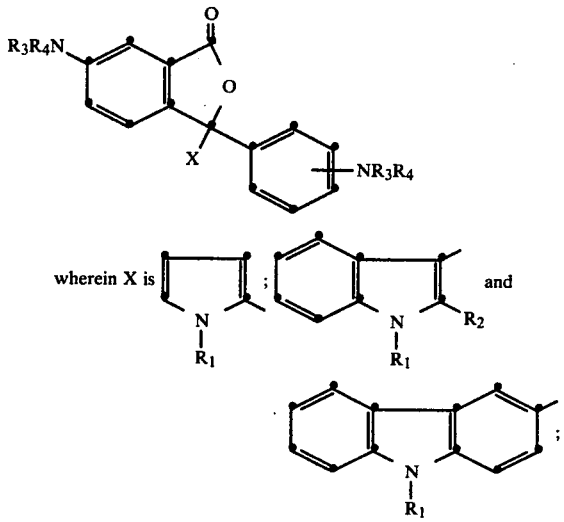

$R_1$ and $R_2$ are alkyl having fewer than five carbon atoms, phenyl or hydrogen; and $R_3$ and $R_4$ are alkyl having fewer than five carbon atoms.

SUMMARY OF THE INVENTION

The present invention provides novel 3-heteroaryl-3-(diphenylamino)phthalides useful as color formers in pressure-sensitive duplicating systems and thermal marking systems. The compounds develop colored images of good to excellent tinctorial strength, and have the advantages of improved light stability, high resistance to sublimation and enhanced solubility in common organic solvents. Certain species are also soluble in water and lower alkanols and are therefore of particular utility as color formers in hectographic or spirit-reproducing copying systems.

In a composition-of-matter aspect the invention relates to a series of 3-heteroaryl-3-[N-($Y_1$-$Y_2$-phenyl)-N-($Y_3$-$Y_4$-phenyl)amino]-$Q_n$-phthalides which are useful as color formers in pressure-sensitive carbonless duplicating systems, thermal marking systems or hectographic copying systems.

In a process aspect the present invention provides a process for preparing 3-heteroaryl-3-[N-($Y_1$-$Y_2$-phenyl)-N-($Y_3$$Y_4$-phenyl)amino]-$Q_n$-phthalides which comprises reacting a 2-(heteroarylcarbonyl)-$Q_n$-benzoic acid with a N-($Y_1$-$Y_2$-phenyl)-N-($Y_3$-$Y_4$-phenyl)amine.

In another process aspect this invention relates to a process for preparing 3-heteroaryl-3-[N-($Y_1$-$Y_2$-phenyl)-N-($Y_3$-$Y_4$-phenyl)amino]-$Q_n$-phthalides which comprises reacting a 2-(heteroarylcarbonyl)-$Q_n$-benzoic acid with an inorganic acid chloride followed by reaction of the product so-obtained with a N-($Y_1$-$Y_2$-phenyl)-N-($Y_3$-$Y_4$-phenyl)amine.

This invention also provides another process for preparing 3-(1-$R_1$-2-$R_2$-$R_3$-3-indolyl)-3-[N-($Y_1$-$Y_2$-phenyl)-N-($Y_3$-$Y_4$-phenyl)amino]-$Q_n$-phthalides which comprises reacting a N-($Y_1$-$Y_2$-phenyl)-N-($Y_3$-$Y_4$-phenyl)-$Q_n$-phthalamic acid with a 1-$R_1$-2-$R_2$-$R_3$-indole.

The present invention provides as articles of manufacture a pressure-sensitive carbonless duplicating system, a thermal marking system and a hectographic copying system each containing a color-forming substance comprising a 3-heteroaryl-3-[N-($Y_1$-$Y_2$-phenyl)-N-($Y_3$-$Y_4$-phenyl)amino]-$Q_n$-phthalide.

DETAILED DESCRIPTION INCLUSIVE OF THE PREFERRED EMBODIMENTS

More specifically, this invention in a composition-of-matter aspect resides in a compound having Formula I

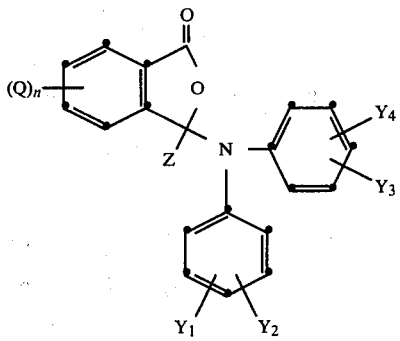

Formula I wherein:

Q is selected from the group consisting of dilower-alkylamino, nitro, halo and COX where X is hydroxyl, benzyloxy, alkoxy having from 1 to 18 carbon atoms or OM where M is an alkali metal cation, an ammonium cation or a mono-, di- or tri-alkylammonium cation having from 1 to 18 carbon atoms;

n is 0; or 1 when Q is di-lower-alkylamino, nitro or COX; or from 1 to 4 when Q is halo;

$Y_1$, $Y_2$, $Y_3$ and $Y_4$ are the same or different and are selected from the group consisting of hydrogen, halo, hydroxyl, lower-alkoxy, alkyl having from 1 to 9 carbon atoms, phenyl-lower-alkyl, COOR$_4$ and NR$_5$R$_6$ where R$_4$ and R$_5$ are hydrogen or lower-alkyl and R$_6$ is hydrogen, lower-alkyl, cycloalkyl having from 5 to 7 carbon atoms, or lower alkanoyl.

Z is selected from the group consisting of

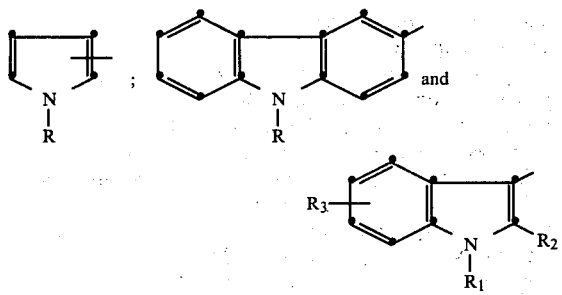

in which:

R is hydrogen or non-tertiary alkyl having from 1 to 4 carbon atoms;

$R_1$ is hydrogen, or non-tertiary alkyl having from 1 to 18 carbon atoms;

$R_2$ is hydrogen, phenyl or non-tertiary alkyl having from 1 to 4 carbon atoms; and $R_3$ is hydrogen, non-tertiary alkyl having from 1 to 4 carbon atoms or non-tertiary alkoxy having from 1 to 4 carbon atoms.

The compounds are useful as color formers in pressure-sensitive carbonless duplicating systems, thermal marking systems and hectographic copying systems.

A particular embodiment sought to be patented resides in a compound having Formula II

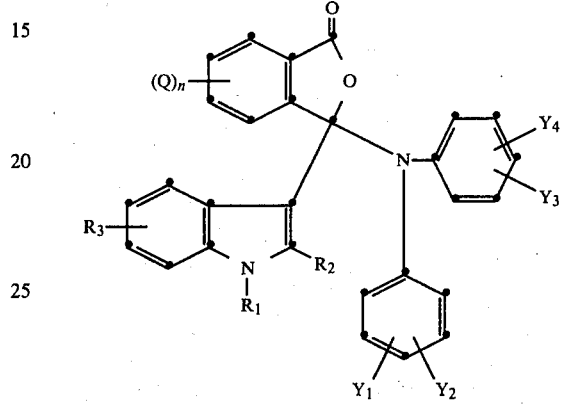

Formula II wherein Q, n, $R_1$, $R_2$, $R_3$, $Y_1$, $Y_2$, $Y_3$ and $Y_4$ have the previously given meanings. Preferred compounds within the ambit of this particular embodiment are those wherein:

(a) n is 0;

(b) n is 1 and Q is COX where X has the previously given meaning; and (c) n is 4 and Q is halo; especially 3-[N-(4-ethoxyphenyl)-N-phenylamino]-3-(1-ethyl-2-methyl-3-indolyl)phthalide, 3-(diphenylamino)-3-(1-ethyl-2-methyl-3-indolyl)phthalide, 3-(1-ethyl-2-methyl-3-indolyl)-3-(N-phenyl-N-m-tolylamino)phthalide 3-(1-ethyl-2-methyl-3-indolyl)-3-[N,N-bis-(3-ethyl-5-nonylphenyl)amino]phthalide, 5-(and 6-)carboxy-3-[N-(4-ethoxyphenyl)-N-phenylamino]-3-(1-ethyl-2-methyl-3-indolyl)phthalide, 3-[N-(4-ethoxyphenyl)-N-phenylamino]-3-(1-ethyl-2-methyl-3-indolyl)-5-(and 6-)methoxycarbonylphthalide, 5-(and 6-)ethoxycarbonyl-3-[N-(4-ethoxyphenyl)-N-phenylamino]-3-(1-ethyl-2-methyl-3-indolyl)phthalide, 3-[N-(4-ethoxyphenyl)-N-phenylamino]-3-(1-ethyl-2-methyl-3-indolyl)-5-(and 6-)-n-octyloxycarbonylphthalide, 5-(and 6-)benzyloxycarbonyl-3-N-[4-(ethoxyphenyl)-N-phenylamino]-3-(1-ethyl-2-methyl-3-indolyl) phthalide, 4,5,6,7-tetrachloro-3-[N-(4-ethoxy-phenyl)-N-phenylamino]-3-(1-ethyl-2-methyl-3-indolyl)phthalide and 3-(1-ethyl-2-methyl-3-indolyl)-3-[N,N-bis-(4-octylphenyl)amino] phthalide.

In one of its process aspects the invention sought to be patented resides in the process which comprises reacting a 2-substituted benzoic acid having Formula III

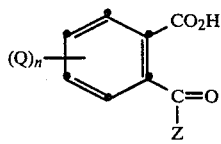

Formula III with a diarylamine having Formula IV

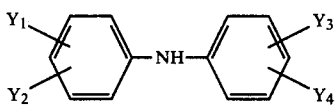

Formula IV in the presence of the anhydride of an alkanoic acid having from 2 to 5 carbon atoms, and an organic base; where in Formulas III and IV Z, n, $Y_1$, $Y_2$, $Y_3$ and $Y_4$ have the previously given meanings and Q is selected from the group consisting of di-lower-alkylamino, nitro, halo and COX where X is hydroxy, benzyloxy or alkoxy having from 1 to 18 carbon atoms.

In another process aspect the invention sought to be patented resides in the process which comprises reacting a 2-substituted benzoic acid of Formula III with an inorganic acid chloride selected from the group consisting of thionyl chloride, phosphorus oxychloride, phosphorus trichloride and phosphorus pentachloride followed by reaction of the resulting product with a diarylamine of Formula IV in the presence of an organic base; where in Formulas III and IV Z, Q, n, $Y_1$, $Y_2$, $Y_3$ and $Y_4$ have the meanings given in the preceding paragraph.

In yet a further process aspect the invention sought to be patented resides in the process which comprises reacting a phthalamic acid having Formula V

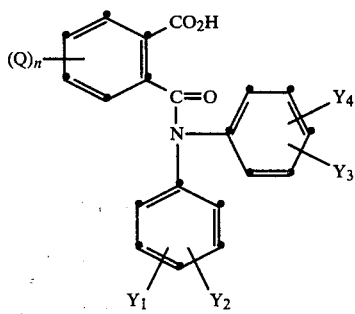

Formula V with an indole having Formula VI

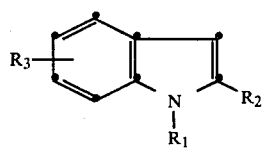

Formula VI in the presence of the anhydride of an alkanoic acid having from 2 to 5 carbon atoms; where in Formulas V and VI Q, n, $Y_1$, $Y_2$, $Y_3$, $Y_4$, $R_1$, $R_2$ and $R_3$ have the above-given meanings.

In an article-of-manufacture aspect the invention sought to be patented resides in a pressure-sensitive carbonless duplicating system, thermal marking system or hectographic copying system containing a color-forming substance comprising a compound having Formula I.

A particular embodiment sought to be patented resides in a pressure-sensitive transfer sheet, adapted for use with a receiving sheet having an electron accepting layer, comprising a support sheet coated on one side with a layer of pressure-rupturable microcapsules, said microcapsules containing a liquid solution of a color forming substance comprising at least one compound having Formula I.

Another particular embodiment sought to be patented resides in a heat responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

Preferred articles within the ambit of the particular embodiments above-described are those wherein the color-forming component comprises a compound having Formula II, especially wherein Formula II:

(a) n is 0;

(b) n is 1 and Q is COX where X is hydroxyl, benzyloxy or alkoxy having from 1 to 18 carbon atoms; and (c) n is 4 and Q is halo.

A further particular embodiment sought to be patented resides in a hectographic or spirit reproducing copying system comprising a transfer sheet coated on one side with a layer containing a color-forming substance comprising at least one compound having Formula I wherein n is 1 and Q is COX where X is OM and M has the previously given meaning.

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However the other above-named halo substituents are also satisfactory.

The terms "lower-alkyl, lower-alkoxy and di-lower-alkylamino" denote saturated, acyclic groups having from 1 to 4 carbon atoms which may be straight or branched as examplified by methyl, ethyl, propyl, isopropyl, butyl, sec-butyl, isobutyl, tert-butyl, methoxy, ethoxy, propoxy, isopropoxy, butoxy, sec-butoxy, isobutoxy, tert-butoxy, dimethylamino, diethylamino, ethylmethylamino, dipropylamino, dibutylamino, isobutylmethylamino, di-tert-butylamino and the like.

As used herein the term "cycloalkyl having from 5 to 7 carbon atoms" includes cyclopentyl, cyclohexyl and cycloheptyl.

The term "lower alkanoyl" denotes saturated acyclic acyl groups having from 1 to 5 carbon atoms which may be straight or branched as exemplified by formyl, acetyl, propionyl, butyryl, isobutyryl, valeryl, 2-methylbutyryl, isovaleryl, pivalyl and the like.

The term "phenyl-lower-alkyl" includes benzyl, 2-phenylethyl, 2-phenylpropyl, 3-phenylpropyl, 1-phenylbutyl, 2,2-dimethyl-2-phenylethyl and the like. If desired the phenyl group may contain a lower alkyl or lower alkoxy substituent.

The term "alkoxy having from 1 to 18 carbon atoms" includes, in addition to the above-noted lower-alkoxy groups, saturated, acyclic, straight or branched-chain groups such as n-pentyloxy, n-hexyloxy, n-heptyloxy, n-octyloxy, n-nonyloxy, n-decyloxy, n-undecyloxy, n-dodecyloxy, n-tridecyloxy, n-tetradecyloxy, n-pentadecyloxy, n-hexahecyloxy, n-heptadecyloxy, n-octadecyloxy, 1-methylpentyloxy, 2,2-dimethylbutyloxy, 2-methylhexyloxy, 1,4-dimethylpentyloxy, 3-ethylpentyloxy, 2-methylheptyloxy, 1-ethylhexyloxy, 2-propylpentyloxy, 2-methyl-3-ethylpentyloxy, 1,3,5-trimethylhexyloxy, 1,5-dimethyl-4-ethylhexyloxy, 5-methyl-2-butylhexyloxy-2-propylnonyloxy, 2-butyloctyloxy, 1,1-dimethylundecyloxy, 2-pentylnonyloxy, 1,2-dimethyltetradecyloxy, 1,1-dimethyl-pentadecyloxy and the like.

As used herein the term "alkyl having from 1 to 9 carbon atoms" denotes saturated monovalent straight or branched chain aliphatic hydrocarbon radicals including methyl, ethyl, propyl, isopropyl, butyl, isobutyl, tert-butyl, amyl, 1-methylbutyl, 3-methylbutyl, hexyl, isohexyl, heptyl, isoheptyl, octyl, isooctyl, 2-ethylhexyl, nonyl, 3-ethylheptyl and the like.

The term "non-tertiary alkyl having from 1 to 18 carbon atoms" includes, in addition to the above-named alkyl groups having from 1 to 9 carbon atoms, excluding of course any tertiary alkyl groups, saturated, monovalent, straight or branched-chain aliphatic hydrocarbon radicals such as n-decyl, n-undecyl, n-dodecyl, n-tridecyl, n-tetradecyl, n-pentadecyl, n-hexadecyl, n-heptadecyl, n-octadecyl, 1,3,5-trimethylhexyl, 1,5-dimethyl-4-ethylhexyl, 5-methyl-2-butylhexyl, 2-propylnonyl, 2-butyloctyl, 2-pentylnonyl, 1,2-dimethyltetradecyl, and the like.

As used herein the term "alkali metal" includes lithium, sodium and potassium.

The term "mono-, di- or tri-alkylammonium cation" includes ammonium cations substituted by from 1 to 3 alkyl groups as above described. The alkyl groups can be the same or different provided the ammonium cation contains no more than 18 carbon atoms. As examples there can be named methylammonium, t-butylammonium, t-octylammonium, n-dodecylammonium, n-octadecylammonium, di-n-butylammonium, di-n-nonylammonium, isopropyl-n-butylammonium, dimethyl-n-butylammonium, triethylammonium, N-ethyl-N,N-diisopropylammonium, tributylammonium, di-n-butyl-n-octylammonium and the like.

Anhydrides of alkanoic acids of two to five carbon atoms include acetic anhydride, propionic anhydride, butyric anhydride, isobutyric anhydride, valeric anhydride, isovaleric anhydride, α-methylbutyric anhydride, pivalic anhydride and the like. Acetic anhydride is preferred because of its low cost and high reactivity, however the other above-named anhydrides are also satisfactory.

Organic bases include pyridine, collidine, trilower-alkyl amines, urea, diarylamines of Formula IV hereinabove and the like. Because of their low cost and ready availability pyridine and urea are preferred.

In accordance with one of the process aspects of this invention the compounds having Formula I are obtained by reacting approximately equimolar amounts of a 2-substituted benzoic acid of Formula III and a diarylamine of Formula IV in the anhydride of an alkanoic acid having from two to five carbon atoms, such as acetic anhydride, with or without an inert diluent and in the presence of an organic base, for example pyridine or urea, at a temperature of from about 0° to 100° C. for from approximately 10 minutes to 24 hours. The reaction is usually carried out in the absence of an inert diluent at about 20° to 40° C. for approximately 0.5 to 2 hours. If desired an excess of the diarylamine reactant can be employed as the organic base. The product thus obtained can be isolated by filtration if it is insoluble in the reaction medium or by dilution of the reaction medium with a miscible solvent in which the product is insoluble such as a lower-alkanol or low molecular weight hydrocarbon for example isopropyl alcohol or hexane or a mixture of these in order to effect precipitation of the product. Alternatively, the reaction mixture can be poured into aqueous base such as dilute ammonium hydroxide, sodium hydroxide, sodium carbonate or sodium bicarbonate and the product extracted with an organic solvent such as benzene or toluene followed by evaporation of the organic solvent leaving the product as a residue. The product once isolated can be purified by conventional means such as trituration or recrystallization from a suitable solvent.

In accordance with a second process aspect of the invention the compounds of Formula I can be prepared in two steps which comprise first reacting a 2-substituted benzoic acid of Formula III with an excess of an inorganic acid chloride such as thionyl chloride, phosphorus oxychloride, phosphorus trichloride or phosphorus pentachloride with or without an inert diluent such as benzene, toluene, chloroform or 1,2-dichloroethane, at 20° to 80° C. for about 0.5 to 2 hours; and following removal of excess inorganic acid chloride, reaction of the resulting product which while not having been isolated is presumed to be a halide having Formula VII

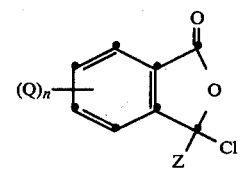

Formula VII in which Q, n and Z have meanings previously given in Formula III, with a diarylamine of Formula IV hereinabove in an inert solvent in the presence of an organic base as previously described at a temperature in the range of 0° to 80° C. for about 1 to 48 hours. The product can be isolated and purified in the manner previously described.

In accordance with a further process aspect of the present invention the compounds having Formula II can be prepared by reacting a phthalamic acid of Formula V with an indole of Formula VI in the anhydride of an alkanoic acid having from two to five carbon atoms, such as acetic anhydride, with or without an inert diluent and optionally in the presence of an organic base, for example pyridine or urea, at a temperature of from about 0° to 100° C. for from approximately 1 to 24 hours. The reaction is usually carried out at about 20° to 40° C. for approximately 2 to 12 hours. The product so-obtained can be isolated and purified in accordance with the above-described procedures.

When preparing compounds of Formula I wherein Q is COX and X is benzyloxy, alkoxy having from 1 to 18 carbon atoms or OM where M is an alkali metal cation, an ammonium cation or a mono-, di- or trialkylammonium cation having from 1 to 18 carbon atoms it is ordinarily preferred to first prepare the compound of Formula I wherein Q is COOH followed by conversion of the carboxyl group to the desired ester, alkali metal salt or ammonium salt in accordance with conventional procedures.

Some of the 2-substituted benzoic acids of Formula I required as starting materials in the preparation of the products of Formula I are known, for example as disclosed in U.S. Pat. No. 3,812,146, issued May 21, 1974, German Offenlegungsschrift 2,423,534, published Dec. 12, 1974, Journal of the Chemical Society 107, 885 (1915) and Chemical Abstracts 83, 77938h (1975). Those which are novel are the invention of Paul J. Schmidt and Nathan N, Crounse and are the subject of commonly assigned U.S. patent application Ser. No. 773,180, filed Mar. 1, 1977. Both known and novel 2-substituted benzoic acids are prepared in similar fashion, i.e., by reacting a phthalic anhydride having Formula VIII

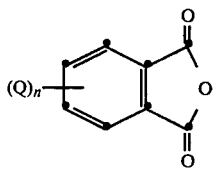

Formula VIII with an appropriate indole of Formula VI or a pyrrole or carbazole of Formula IX and X, respectively,

 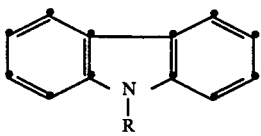

Formula IX    Formula X

Q and n in Formula VIII having the meanings given above in Formula III and R in Formulas IX and X having the previously given meanings, in the presence of a Lewis acid, for example, aluminum chloride or zinc chloride, and with a diluent such as benzene, chlorobenzene or o-dichlorobenzene at a temperature of about 0° to 100° C. The reaction is conveniently carried out in benzene in the presence of aluminum chloride at about 0° to 25° C. Alternatively, the more reactive indoles (Formula VI) can be reacted with the phthalic anhydrides (Formula VIII) in the absence of a Lewis acid by simply heating the reactants together in an inert solvent at about 80° to 150° C.

It will, of course, be appreciated that reaction of an unsymmetrically substituted phthalic anhydride (Formula VIII) with an indole, pyrrole or carbazole (Formulas VI, IX or X) can produce isomers of a mixture of isomers of 2-(heteroarylcarbonyl) benzoic acids (Formula III). For example, reaction of a 3-substituted phthalic anhydride (Formula VIII where n is 1 and Q occupies position 3) with an indole, pyrrole or carbazole can produce either a 3- or 6-substituted 2-(heteroarylcarbonyl) benzoic acid (Formula III where n is 1 and Q occupies either position 3 or position 6) of a mixture of these. Similarly a 4-substituted phthalic anhydride (Formula VIII where n is 1 and Q occupies position 4) can produce either a 4- or a 5-substituted 2-(heteroarylcarbonyl)-benzoic acid (Formula III, where n is 1 and Q occupies position 4 or position 5) or a mixture of these. The mixtures of isomeric 2-(heteroarylcarbonyl)benzoic acids can be separated by conventional means such as fractional crystallization or chromatography. Alternatively, the isomeric mixtures can be reacted directly with appropriate diarylamines of Formula IV to produce isomeric mixtures of phthalides of Formula I. Thus reaction of a mixture of 3- and 6-substituted 2-(heteroarylcarbonyl)benzoic acids (Formula III where n is 1 and Q occupies position 3 or 6) with a diarylamine of Formula IV will produce a mixture of 4- and 7-substituted phthalides (Formula I where n is 1 and Q occupies position 4 or 7); and in like fashion a mixture of 4- and 5-substituted 2-(heteroarylcarbonyl)benzoic acids (Formula III where n is 1 and Q occupies position 4 or 5) will produce a mixture of 5- and 6-substituted phthalides (Formula I where n is 1 and Q occupies position 5 or 6). The mixtures of phthalides can, if desired, be separated by conventional means or simply and preferably used as mixtures in the practice of this invention.

The diarylamines of Formula IV which are also required as starting materials in the processes of the invention belong to a well known class of compounds and are either commercially available or readily obtained by conventional procedures well known in the art.

The novel compounds of Formula I hereinabove are essentially colorless in the depicted form. When contacted with an acidic medium, for example silica gel or one of the types ordinarily employed in pressure-sensitive carbonless duplicating systems such as silton clay or phenolic resins the compounds of Formula I develop a yellow to black colored image of good to excellent tinctorial strength, and possessing excellent light stability, resistance to sublimation and xerographic copiability. The compounds are thus highly suitable for use as colorless precursors, that is color-forming substances in pressure-sensitive carbonless duplicating systems. The compounds which produce a yellow to red color can be used as toners in admixture with other color formers to produce images of a neutral shade which desirably are readily copiable by xerographic means. The compounds of Formula I wherein at least one of $Y_1$ and $Y_2$ and at least one of $Y_3$ and $Y_4$ are simultaneously di-lower-alkylamino develop a brown to grape image when contacted with an acidic medium and are accordingly of particular value as color precursors. Moreover, the compounds of Formula I, in particular those wherein n is 1, Q is COX and X is alkoxy having from 1 to 18 carbon atoms, or those where one or more of $Y_1$, $Y_2$, $Y_3$ and $Y_4$ are alkyl of 1 to 9 carbon atoms, have enhanced solubility in common and inexpensive organic solvents such as odorless mineral spirits, kerosene, vegetable oils and the like; and those wherein n is 1, Q is COX and X is OM in which M has the previously given meaning are soluble in water and lower-alkanols thereby avoiding the need for more expensive, specialized solvents such as polyhalogenated or alkylated biphenyls which have ordinarily been used to prepare microencapsulated solutions of the color formers of the prior art.

The compounds of this invention may be incorporated in any of the commercially accepted systems known in the carbonless duplicating art. A typical technique for such application is as follows. Solutions containing one or more colorless precursor compounds of Formula I, optionally in admixture with other color formers, in suitable solvents are microencapsulated by well-known procedures for example as described in U.S. Pat. No. 3,649,649. The microcapsules are coated on the reverse side of a transfer sheet with the aid of a suitable binder and the coated transfer sheet is then assembled in a manifold with the microcapsule coated side in contact with a receiving sheet coated with an electron accepting substance, for example, silton clay or a phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms a yellow to red colored image of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers such as described in U.S. Pat. No. 3,539,375, that is, papers which produce a colored image when contacted with a heated stylus or heated type, for example, bisphenol A, heating of the mixture produces a colored image of varying shades from yellow to purple depending on the particular compound of the invention employed. The ability of the compounds of Formula I to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

The compounds of this invention which are soluble in water and lower-alkanols may be incorporated in any of the commercial hectographic or spirit-reproducing copying systems such as described in British Pat. No. 1,427,318 published Mar. 10, 1976. In such systems a transfer sheet coated on one side with a layer containing one or more water- or lower alkanol-soluble color formers of Formula I is placed with its coated surface against one surface of a master paper which is then typed, written or marked on, causing transfer of the coating as a substantially colorless reverse image to the master paper at the points where the transfer sheet and master paper have been pressed together. The master paper is then brought into contact with a succession of sheets of paper moistened with a suitable spirit-reproducing fluid such as ethanol. The fluid dissolves a part of the color former and transfers it to each paper sheet where it combines with an electron-accepting substance, to give a yellow to red colored image which duplicates the original typing or writing on the master paper.

The molecular structures of the compounds of this invention were assigned on the basis of the modes of synthesis, elemental analysis and study of their infrared, nuclear magnetic resonance, and mass spectra.

The following examples will further illustrates the invention without, however, limiting it thereto.

EXAMPLE 1

A. A mixture containing 24 g. of 2-(1-ethyl-2-methyl-3-indolylcarbonyl)benzoic acid, 16.5 g. of 4-ethoxy-N-phenylaniline, 7 ml. of pyridine and 70 ml. of acetic anhydride was stirred 1 hr. at room temperature. Dilution with 30 ml. of 2-propanol and 100 ml. of ligroin produced no precipitate. The reaction mixture was therefore poured into 10% aqueous ammonia and the product was extracted with toluene. The organic extracts were washed with water and saturated aqueous sodium chloride and evaporated to dryness under vacuum. Trituration of the residue with ligroin afforded 25.3 g. of 3-[N-(4-ethoxyphenyl)-N-phenylamino]-3-(1-ethyl-2-methyl-3-indolyl)phthalide, m.p. 110°–135° C. Recrystallization of an analytical sample from 2-propanol-ligroin provided colorless crystals, m.p. 161°–163° C. A toluene solution of the product contacted with acidic clay or phenolic resin developed a yellow colored image.

B. A mixture containing 7.86 g. (0.02 mole) of 2-(1-ethyl-2-methyl-3-indolylcarbonyl)benzoic acid, 6.38 g. (0.03 mole) of 4-ethoxy-N-phenylaniline and 12 ml. of acetic anhydride was stirred overnight at room temperature and then poured into 200 ml. of 10% aqueous sodium hydroxide and 100 ml. of toluene. After stirring 1 hr. the layers were separated. The toluene layer was dried over anhydrous sodium sulfate, treated with decolorizing carbon and filtered. The filtrate was concentrated to 50 ml. and slowly diluted with 900 ml. of hexane. The precipitated product was collected, washed with hexane and dried to give 6.0 g. of product essentially identical to the product of part A above.

EXAMPLE 2

A. A mixture containing 3.1 g. of 2-(1-ethyl-2-methyl-3-indolylcarbonyl)benzoic acid, 5 g. of 3,3'-diethyl-5,5'-dinonyldiphenylamine, 10 ml. of acetic anhydride and 1 ml. of pyridine was stirred 1 hr. at room temperature and then poured into 10% aqueous sodium hydroxide and the product extracted with toluene. The toluene extracts were dried over anhydrous sodium sulfate and evaporated to dryness under vacuum. Trituration of the residue with ligroin and 2-propanol afforded 0.8 g. of 3-[N,N-bis-(3-ethyl-5-nonylphenyl)amino]-3-(1-ethyl-2-methyl-3-indolyl)phthalide, m.p. 76°–90° C. (dec.). A toluene solution of the product contacted with acidic clay or phenolic resin developed a red colored image.

B. A mixture containing 6.2 g. of 2-(1-ethyl-2-methyl-3-indolylcarbonyl)benzoic acid, 9.3 g. of 3,3'-diethyl-5,5'-di-nonyldiphenylamine, 25 ml. of acetic anhydride and 1 g. of urea was stirred 2 hrs. at room temperature and then poured into 5% aqueous ammonium hydroxide and extracted with toluene. The organic extracts were dried over anhydrous sodium sulfate and evaporated to dryness under vacuum. The residue was triturated with cyclohexane to give 4.96 g. of product essentially identical to the product of part A above.

EXAMPLE 3

A. A stirred solution containing 48.0 g. (0.250 mole) of trimellitic anhydride and 45.0 g. (0.314 mole) of 1-ethyl-2-methylindole in 350 ml. of 1,2-dichloroethane was heated 2 hrs. under reflux. The reaction mixture was allowed to cool to room temperature and the precipitated solid was collected, washed with 1,2-dichloroethane and dried to give 66.0 g. of a mixture of 4- and 5-carboxy-2-(1-ethyl-2-methyl-3-indolylcarbonyl)benzoic acid, m.p. 198°–201° C. This material was used in subsequent reactions without further purification.

B. A mixture containing 7.0 g. of 4-(and 5-)carboxy-2-(1-ethyl-2-methyl-3-indolylcarbonyl)benzoic acid, 4.3 g. of 4-ethoxy-N-phenylaniline, 25 ml. of acetic anhydride and 2 ml. of pyridine was stirred 2 hrs. at room temperature. Dilution with 20 ml. of 2-propanol and 100 ml. of ligroin produced no precipitate. The mixture was therefore poured into toluene and the product extracted with 5% aqueous ammonia. The aqueous alkaline extracts were neutralized with 3 N hydrochloric acid. The resulting precipitate was collected, washed with water and dried to give 5.6 g. of 5-(and 6-)carboxy-3-[N-(4-ethoxyphenyl)-N-phenylamino]-3-(1-ethyl-2-methyl-3-indolyl)phthalide, m.p. 145°–148° C.

C. To a stirred solution containing 2 g. of the above acid in 30 ml. of acetone was added 2 ml. t-octylamine. After stirring 10 minutes the mixture was diluted with 200 ml. of hexane. The solvents were decanted and the residue was triturated with hexane to give 1.8 g. of t-octylammonium 3-[N-(4-ethoxyphenyl)-N-phenylamino]-3-(1-ethyl-2-methyl-3-indolyl)phthalide-5-(and 6-)carboxylate, m.p. 141° C. (dec.).

EXAMPLE 4

To a refluxing mixture containing 5.5 g. of 5-(and 6-)carboxy-3-[N-(4-ethoxyphenyl)-N-phenylamino]-3-(1-ethyl-2-methyl-3-indolyl)phthalide, 3 g. of potassium carbonate and 150 ml. of acetone was added 4 g. of dimethylsulfate. After heating 1 hr. under reflux the mixture was poured into 300 ml. of 5% aqueous ammonia and extracted with 400 ml. of toluene. The toluene extracts were washed with water and saturated aqueous sodium chloride and evaporated to dryness. Trituration of the residue with ligroin afforded 0.6 g. of 5-(and 6-)methoxycarbonyl-3-[N-(4-ethoxyphenyl)-N-phenylamino]-3-(1-ethyl-2-methyl-3-indolyl)phthalide as a tan solid, m.p. 79°–84° C. (dec.). A toluene solution of the product contacted with acidic clay or phenolic resin developed a yellow-orange colored image.

EXAMPLE 5

A mixture containing 3.0 g. of 5-(and 6-)carboxy-3-[N-(4-ethoxyphenyl)-N-phenylamino]-3-(1-ethyl-2-methyl-3-indolyl)phthalide, 3 ml. of 25% aqueous sodium hydroxide and 50 ml. of hexamethylphosphoramide was stirred 1 hr. at room temperature and then treated with 3 ml. of ethyl iodide. After stirring at room temperature another 2 hrs. the reaction mixture was poured into water and the product extracted with toluene. The toluene extracts were washed with water and saturated aqueous sodium chloride, dried over anhydrous sodium sulfate and evaporated to dryness under vacuum. The residue was triturated with ligroin to give 0.2 g. of 5-(and 6-)ethoxycarbonyl-3-[N-(4-ethoxyphenyl)-N-phenylamino]-3-(1-ethyl-2-methyl-3-indolyl)phthalide as a light brown solid, m.p. 86°–93° C. (dec.). A toluene solution of the product contacted with acidic clay or phenolic resin developed an orange colored image.

EXAMPLE 6

A mixture containing 5.5 g. of 5-(and 6-)carboxy-3-[N-(4-ethoxyphenyl)-N-phenylamino]-3-(1-ethyl-2-methyl-3-indolyl)phthalide, 8 ml. of n-octyl bromide, 6 g. of potassium carbonate and 150 ml. of acetone was heated under reflux overnight. The reaction mixture was then poured into 5% aqueous ammonia and the product extracted with toluene. The toluene extracts were washed with water and saturated aqueous sodium chloride, dried over anhydrous sodium sulfate and evaporated to dryness under reduced pressure. Excess n-octyl bromide was removed from the residue by vacuum distillation leaving as an oil 5-(and 6-)n-octyloxycarbonyl-3-[N-(4-ethoxyphenyl)-N-phenylamino]-3-(1-ethyl-2-methyl-3-indolyl)phthalide. A toluene solution of the product contacted with acidic clay or phenolic resin developed an orange colored image.

EXAMPLE 7

To a mixture containing 3.0 g. of 5-(and 6-)carboxy-3-[N-(4-ethoxyphenyl)-N-phenylamino]-3-(1-ethyl-2-methyl-3-indolyl)phthalide, 3.0 g. of potassium carbonate and 100 ml. of N,N-dimethylformamide was added 2.0 g. of α-bromotoluene. After stirring 10 min. the reaction mixture was poured into ice-water and the resulting precipitate was collected and dissolved in acetone. The acetone solution was evaporated to dryness and the residue was triturated with ligroin to give 5-(and 6-)benzyloxycarbonyl-3-[N-(4-ethoxyphenoyl)-N-phenylamino]-3-(1-ethyl-2-methyl-3-indolyl)phthalide as a pale orange solid, m.p. 80°–85° C. A toluene solution of the product contacted with acidic clay or phenolic resin developed an orange-yellow colored image.

EXAMPLE 8

A mixture containing 4.5 g. of 3,4,5,6-tetrachloro-2-(1-ethyl-2-methyl-3-indolylcarbonyl)benzoic acid, 1.0 ml. of thionyl chloride and 200 ml. of 1,2-dichloroethane was heated up to the reflux temperature, then cooled to 30° C. and treated with a solution containing 2.1 g. of 4-ethoxy-N-phenylaniline in 20 ml. of 1,2-dichloroethane. After stirring overnight at room temperature the reaction mixture was poured into 5% aqueous ammonia and the product extracted with 1,2-dichloroethane. The organic extracts were washed with water and saturated aqueous sodium chloride and evaporated to dryness. The residue was triturated with cyclohexane to give 3.1 g. of 4,5,6,7-tetrachloro-3-[N-(4-ethoxyphenyl)-N-phenylamino]-3-(1-ethyl-2-methyl-3-indolyl)phthalide, m.p. 182°–188° C. The infrared spectrum indicated this material to be contaminated with unreacted 3,4,5,6-tetrachloro-2-(1-ethyl-2-methyl-3-indolylcarbonyl)benzoic acid. Evaporating the triturant to dryness and triturating the residue successively from ligroin and acetone afforded 0.4 g. of the pure phthalide, m.p. 193°–194° C. (dec.). A toluene solution of the product contacted with acidic clay or phenolic resin developed an orange colored image.

EXAMPLE 9

A. Following a procedure similar to that described in Example 1A but employing 3.1 g. of 2-(1-ethyl-2-methyl-3-indolylcarbonyl)benzoic acid and 1.8 g. of diphenylamine there was obtained 0.78 g. of 3-(1-ethyl-2-methyl-3-indolyl)-3-(diphenylamino)phthalide, m.p. 125°–130° C. (dec.). A toluene solution of the product contacted with acidic clay or phenolic resin developed a yellow colored image.

B. A mixture containing 3.0 g. of N,N-diphenylphthalamic acid, 1.6 g. of 1-ethyl-2-methylindole, 7 ml. of acetic anhydride and 0.5 ml. of pyridine was stirred several hours at room temperature. The reaction mixture was filtered to remove unreacted N,N-diphenylphthalamic acid. The filtrate was analyzed by thin layer chromatography and shown to contain the desired 3-(1-ethyl-2-methyl-3-indolyl)-3-(diphenylamino)phthalide identical to the product of part A above contaminated with some 3,3-bis-(1-ethyl-2-methyl-3-indolyl)phthalide.

C. The reaction of part B above was carried out in the absence of pyridine. The reaction mixture was poured into 5% aqueous ammonia and the product extracted with toluene. The toluene extracts were washed with water and saturated aqueous sodium chloride and evaporated to dryness. The residue was essentially identical to the product of part B above as indicated by thin layer chromatography.

EXAMPLE 10

A mixture containing 7.0 g. of 2-(1-ethyl-2-methyl-3-indolylcarbonyl)-4-(and 5-)nitrobenzoic acid, 4.4 g. of 4-ethoxy-N-phenylaniline, 10 ml. of acetic anhydride and 2 ml. of pyridine was stirred 2 hrs. at room temperature. The reaction mixture was diluted with 10 ml. of 2-propanol and 50 ml. of ligroin to precipitate 3.73 g. of unreacted 2-(1-ethyl-2-methyl-3-indolylcarbonyl)-4-(and 5-)nitrobenzoic acid. The filtrate was poured into 5% aqueous ammonia and the product extracted with toluene. The toluene extracts were washed with water and saturated aqueous sodium chloride and evaporated to dryness under vacuum. The residue was triturated successively with ligroin and 2-propanol to give 1.4 g. of 3-[N-(4-ethoxyphenyl)-N-phenylamino]-3-(1-ethyl-2-methyl-3-indolyl)-5-(and 6-)nitrophthalide, m.p. 171°–173° C. A toluene solution of the product contacted with acidic clay or phenolic resin developed an orange colored image.

EXAMPLE 11

Following a procedure similar to that described in Example 1A but employing 3.1 g. of 2-(1-ethyl-2-methyl-3-indolylcarbonyl)benzoic acid and 2.0 g. of N-phenyl-m-toluidine there was obtained 0.99 g. of 3-(1-ethyl-2-methyl-3-indolyl)-3-[N-m-tolyl-N-phenylamino]phthalide, m.p. 171°–174° C. A toluene solution of the product contacted with acidic clay or phenolic resin developed a yellow colored image.

EXAMPLE 12

Following a procedure similar to that described in Example 1A but employing 10.8 g. of 2-(2-methyl-3-indolylcarbonyl)benzoic acid and 7.5 g. of 4-ethoxy-N-phenylaniline there was obtained 10.9 g. of 3-[N-(4-ethoxyphenyl)-N-phenylamino]-3-(2-methyl-3-indolyl)phthalide, m.p. 66°–75° C. (dec.). A toluene solution of the product contacted with acidic clay or phenolic resin developed an orange-yellow colored image.

EXAMPLE 13

Following a procedure similar to that described in Example 1A but employing 2.8 g. of 2-(2-methyl-3-indolylcarbonyl)benzoic acid and 2.5 g. of 4-isopropoxy-N-phenylaniline there was obtained 3.36 g. of 3-[N-(4-isopropoxyphenyl)-N-phenylamino]-3-(2-methyl-3-indolyl)phthalide, m.p. 103°–125° C. (dec.). A toluene solution of the product contacted with acidic clay or phenolic resin developed a yellow colored image.

EXAMPLE 14

A. To a stirred mixture containing 7.4 g. of phthalic anhydride and 16.0 g. of 1-butyl-2-methylindole at 0°–5° C. was added portionwise 13.3 g. of aluminum chloride. The mixture was diluted with 50 ml. of benzene and stirred overnight at room temperature. The reaction mixture was poured into 200 ml of 5% hydrochloric acid and the product extracted with benzene. The benzene extracts were shaken with dilute aqueous potassium hydroxide. The aqueous alkaline layer was separated, cooled with ice and brought to pH 4 with acetic acid. The precipitated product was collected and dried to give 2-(1-butyl-2-methyl-3-indolylcarbonyl)benzoic acid, m.p. 88°–92° C.

B. Following a procedure similar to that described in Example 1A but employing 3.4 g. of 2-(1-butyl-2-methyl-3-indolylcarbonyl)benzoic acid and 2.2 g. of 4-ethoxy-N-phenylaniline there was obtained 3.42 g. of 3-(1-butyl-2-methyl-3-indolyl)-3-[N-(4-ethoxyphenyl)-N-phenylamino]phthalide, m.p. 54°–92° C. A toluene solution of the product contacted with acidic clay or phenolic resin developed a yellow-orange colored image.

EXAMPLE 15

A. Following a procedure similar to that described in Example 14A but employing 7.4 g. of phthalic anhydride and 16.0 g. of 1-n-octyl-2-methylindole there was obtained 6.9 g. of 2-(1-n-octyl-2-methyl-3-indolylcarbonyl)benzoic acid, m.p. 121°–123° C.

B. Following a procedure similar to that described in Example 1A but employing 3.9 g. of 2-(1-n-octyl-2-methyl-3-indolylcarbonyl)benzoic acid and 2.2 g. of 4-ethoxy-N-phenylaniline there was obtained 3-[N-(4-ethoxyphenyl)-N-phenylamino]-3-(1-n-octyl-2-methyl-3-indolyl)phthalide. A toluene solution of the product contacted with acidic clay or phenolic resin developed a yellow-orange colored image.

EXAMPLE 16

A. A mixture containing 5.0 g. of phthalic anhydride, 5.0 g. of 2,5-dimethylindole and 30 ml. of 1,2-dichloroethane was heated under reflux for 20 hours. The reaction mixture was cooled and the resulting precipitate was collected, washed with 1,2-dichloroethane and dried to give 3.8 g. of 2-(2,5-dimethyl-3-indolylcarbonyl)benzoic acid, m.p. 198°–200° C. (dec.).

B. A mixture containing 1.4 g. of 2-(2,5-dimethyl-3-indolylcarbonyl)benzoic acid, 1.3 g. of 4-isopropoxy-N-phenylaniline, 8 ml. of acetic anhyride and 1 ml. of pyridine was stirred one hour at room temperature. The reaction mixture was then diluted with 10 ml. of 2-propanol and 20 ml. of ligroin and stirred an additional 10 minutes. The precipitated solids were collected, washed with a mixture of 2-propanol and ligroin and dried to give 0.94 g. of 3-(N-(4-isopropoxyphenyl)-N-phenylamino]-3-(2,5-dimethyl-3-indolyl)phthalide, m.p.

145°-157° C. (dec.). A toluene solution of the product contacted with acidic clay or phenolic resin developed a yellow colored image.

EXAMPLE 17

A. Following a procedure similar to that described in Example 16A but employing 10 g. of phthalic anhydride and 10 g. of 5-methoxy-2-methylindole there was obtained 4.6 g. of 2-(5-methoxy-2-methyl-3-indolylcarbonyl)benzoic acid, m.p. 202°-203° C. (dec.).

B. Following a procedure similar to that described in Example 1A but employing 1.5 g. of 2-(5-methoxy-2-methyl-3-indolylcarbonyl)benzoic acid and 1.0 g. of 4-ethoxy-N-phenylaniline there was obtained 2.35 g. of 3-[N-(4-ethoxyphenyl)-N-phenylamino]-3-(5-methoxy-2-methyl-3-indolyl)phthalide, m.p. 68°-75° C. (dec.). A toluene solution of the product contacted with acidic clay developed a yellow colored image and when contacted with phenolic resin developed a yellow-orange colored image.

EXAMPLE 18

A. To a stirred mixture of 14.8 g. of phthalic anhydride, 16.2 g. of N-methylpyrrole and 50 ml. of chlorobenzene at 0°-5° C. was added portionwise over 1.25 hrs. 39.0 g. of aluminum chloride. The temperature was maintained at 2°-5° C. throughout the addition. After diluting with an additional 20 ml. of chlorobenzene the reaction mixture was allowed to stand over a weekend. Excess water was added and the mixture was stirred. The solids were allowed to settle and the supernatant water-chlorobenzene mix was decanted. The residue was taken up in 50 ml. of 5% aqueous sodium hydroxide. The resulting solution was filtered and the filtrate was acidified to pH 3 with dilute hydrochloric acid. The precipitated yellow solid was collected and dried to give 9.46 g. of 2-(N-methyl-2-(and 3-)pyrrolylcarbonyl)benzoic acid, m.p. 165°-167° C.

B. Following a procedure similar to that described in Example 1A but employing 2.3 g. of 2-(N-methyl-2-(and 3-)-pyrrolylcarbonyl)benzoic acid and 2.2 g. of 4-ethoxy-N-phenylaniline there was obtained 1.6 g. of 3-[N-(4-ethoxyphenyl)-N-phenylamino]-3-(N-methyl-2-(and 3-)pyrrolyl)phthalide, m.p. 115°-134° C. A toluene solution of the product contacted with acidic clay or phenolic resin developed a yellow colored image.

EXAMPLE 19

Following a procedure similar to that described in Example 1A but employing 3.43 g. of 2-(9-ethyl-3-carbazolylcarbonyl)benzoic acid and 2.13 g. of 4-ethoxy-N-phenylaniline there was obtained 0.73 g. of 3-[N-(4-ethoxyphenyl)-N-phenylamino]-3- (9-ethyl-3-carbazolyl)phthalide, m.p. 75°-85° C. (dec.). A toluene solution of the product contacted with acidic clay or phenolic resin developed a yellow-orange colored image.

It is contemplated that by following procedures similar to those described in the foregoing examples but employing the appropriate 2-(3-indolylcarbonyl)benzoic acids of Formula III and appropriately substituted diarylamines of Formula IV there will be obtained the phthalides of Formula II, Examples 20-44, presented in Table A hereinbelow.

TABLE A

Phthalides of Formula II

| Ex. | Q | n | $R_1$ | $R_2$ | $R_3$ |
|---|---|---|---|---|---|
| 20 | 5-$(CH_3)_2N$ | 1 | n-$C_{18}H_{37}$ | $CH_3$ | H |
| 21 | 6-$(C_2H_5)_2N$ | 1 | n-$C_{14}H_{29}$ | $CH_3$ | H |
| 22 | 6-(n-$C_4H_9)_2N$ | 1 | $CH_3$ | $C_6H_5$ | H |
| 23 | 4-$NO_2$ | 1 | $(CH_3)_2CH(CH_2)_8$ | H | H |
| 24 | 5-Br | 1 | $C_2H_5$ | $CH_3$ | 5-$(CH_3)_2CHCH_2$ |
| 25 | 6-F | 1 | $C_2H_5$ | $C_2H_5$ | 6-$C_2H_5$ |
| 26 | 7-Cl | 1 | n-$C_6H_{13}$ | $CH_3$ | H |
| 27 | Br | 4 | H | $CH_3$ | 5-$(CH_3)_2CHO$ |
| 28 | I | 4 | $C_2H_5$ | $CH_3$ | 6-$CH_3O$ |
| 29 | F | 4 | $C_2H_5$ | $CH_3$ | 4-$CH_3$ |
| 30 | 4,7-$(Cl)_2$ | 2 | n-$C_3H_7$ | $CH_3$ | 7-$C_2H_5O$ |
| 31 | 5,6-$(Br)_2$ | 2 | $CH_3$ | $CH_3$ | 5-n-$C_3H_7$ |
| 32 | 4,5,7-$(Cl)_3$ | 3 | $C_2H_5$ | $CH_3$ | H |
| 33 | 6-$CO_2$-n-$C_{18}H_{37}$ | 1 | $C_2H_5$ | $CH_3$ | H |
| 34 | 5-$CO_2$-$(CH_2)_8CH(CH_3)_2$ | 1 | $C_2H_5$ | $CH_3$ | H |
| 35 | 6-$CO_2$-n-$C_4H_9$ | 1 | $CH_3$ | $CH_3$ | 5-n-$C_4H_9O$ |
| 36 | 5-$CO_2$-n-$C_{14}H_{29}$ | 1 | $C_2H_5$ | $CH_3$ | H |
| 37 | 5-$CO_2^\ominus Na^\oplus$ | 1 | H | H | H |
| 38 | 6-$CO_2^\ominus NH_4^\oplus$ | 1 | $CH_3$ | $CH_3$ | H |
| 39 | 6-$CO_2^\ominus HN^\oplus(C_2H_5)_3$ | 1 | $C_2H_5$ | $CH_3$ | H |
| 40 | 6-$CO_2^\ominus H_2N^\oplus$(n-$C_4H_9)_2$ | 1 | $C_2H_5$ | $CH_3$ | H |
| 41 | 5-$CO_2^\ominus C_2H_5N^\oplus H(i-C_3H_7)_2$ | 1 | H | $CH_3$ | 6-$CH_3$ |
| 42 | 6-$CO_2^\ominus H_3N^\oplus$-n-$C_{18}H_{37}$ | 1 | $C_2H_5$ | $CH_3$ | H |
| 43 | 5-$CO_2^\ominus HN^\oplus$-(n-$C_4H_9)_3$ | 1 | $C_2H_5$ | $CH_3$ | 6-$CH_3O$ |
| 44 | 6-$CO_2^\ominus$n-$C_8H_{17}N^\oplus H$(n-$C_4H_9)_2$ | 1 | $CH_3$ | $CH_3$ | H |
| 45 | — | 0 | $C_2H_5$ | $CH_3$ | H |
| 46 | — | 0 | $C_2H_5$ | $CH_3$ | H |
| 47 | — | 0 | $C_2H_5$ | $CH_3$ | H |
| 48 | 5-$CO_2C_2H_5$ | 1 | $CH_3$ | $CH_3$ | H |
| 49 | 6-$CO_2CH_3$ | 1 | $C_2H_5$ | $CH_3$ | H |
| 50 | — | 0 | $C_2H_5$ | $CH_3$ | H |
| 51 | — | 0 | $C_2H_5$ | $CH_3$ | H |
| 52 | — | 0 | $C_2H_5$ | $CH_3$ | H |
| 53 | Cl | 4 | $CH_3$ | $CH_3$ | 6-$CH_3$ |

| Ex. | Q | n | $Y_1$ | $Y_2$ | $Y_3$ | $Y_4$ |
|---|---|---|---|---|---|---|
| 20 | 5-$(CH_3)_2N$ | 1 | H | H | 4-OH | H |
| 21 | 6-$(C_2H_5)_2N$ | 1 | H | H | 3-Cl | H |

TABLE A-continued

Phthalides of Formula II

| # | | | | | | |
|---|---|---|---|---|---|---|
| 22 | 6-(n-C$_4$H$_9$)$_2$N | 1 | H | H | 2-C$_2$H$_5$ | H |
| 23 | 4-NO$_2$ | 1 | H | H | 3-I | H |
| 24 | 5-Br | 1 | H | H | 4-Br | H |
| 25 | 6-F | 1 | H | H | 3-(CH$_3$)$_3$C | H |
| 26 | 7-Cl | 1 | 2-CH$_3$ | H | 4-CH$_3$O | H |
| 27 | Br | 4 | 3-Br | H | 5-Br | H |
| 28 | I | 4 | H | H | 2-F | H |
| 29 | F | 4 | 2-Cl | H | 4-F | H |
| 30 | 4,7-(Cl)$_2$ | 2 | 3-CH$_3$O | H | 3-CH$_3$O | H |
| 31 | 5,6-(Br)$_2$ | 2 | 3-CH$_3$ | 4-CH$_3$ | 3-CH$_3$ | 4-CH$_3$ |
| 32 | 4,5,7-(Cl)$_3$ | 3 | 3-n-C$_4$H$_9$O | H | 3-n-C$_4$H$_9$O | H |
| 33 | 6-CO$_2$-n-C$_{18}$H$_{37}$ | 1 | 2-Cl | 4-Cl | 2-Cl | 4-Cl |
| 34 | 5-CO$_2$-(CH$_2$)$_8$CH(CH$_3$)$_2$ | 1 | H | H | H | H |
| 35 | 6-CO$_2$-n-C$_4$H$_9$ | 1 | H | H | 4-n-C$_6$H$_{13}$ | H |
| 36 | 5-CO$_2$-n-C$_{14}$H$_{29}$ | 1 | H | H | 4-C$_2$H$_5$O | H |
| 37 | 5-CO$_2^\ominus$Na$^\oplus$ | 1 | H | H | 4-C$_2$H$_5$O | H |
| 38 | 6-CO$_2^\ominus$NH$_4^\oplus$ | 1 | H | H | 3-CH$_3$ | H |
| 39 | 6-CO$_2^\ominus$HN$^\oplus$(C$_2$H$_5$)$_3$ | 1 | H | H | 4-(CH$_3$)$_2$CHO | H |
| 40 | 6-CO$_2^\ominus$H$_2$N$^\oplus$(n-C$_4$H$_9$)$_2$ | 1 | H | H | H | H |
| 41 | 5-CO$_2^\ominus$C$_2$H$_5^\oplus$NH(i-C$_3$H$_7$)$_2$ | 1 | H | H | 4-C$_2$H$_5$O | H |
| 42 | 6-CO$_2^\ominus$H$_3$N$^\oplus$-n-C$_{18}$H$_{37}$ | 1 | H | H | 4-Cl | H |
| 43 | 5-CO$_2^\ominus$H$^\oplus$N-(n-C$_4$H$_9$)$_3$ | 1 | H | H | 4-CH$_3$O | H |
| 44 | 6-CO$_2^\ominus$n-C$_8$H$_{17}$N$^\oplus$H(n-C$_4$H$_9$)$_2$ | 1 | H | H | 4-C$_2$H$_5$O | H |
| 45 | — | 0 | 4-NH$_2$ | H | 4-NH$_2$ | H |
| 46 | — | 0 | 4-NHCOC$_4$H$_9$ | H | H | H |
| 47 | — | 0 | 4-NHC$_4$H$_9$ | H | 4-NHC$_4$H$_9$ | H |
| 48 | 5-CO$_2$C$_2$H$_5$ | 1 | 2-CO$_2$C$_4$H$_9$ | H | H | H |
| 49 | 6-CO$_2$CH$_3$ | 1 | 4-CO$_2$C$_2$H$_5$ | H | H | H |
| 50 | — | 0 | 4-CH$_2$C$_6$C$_6$H$_5$ | H | H | H |
| 51 | — | 0 | 4-CH(CH$_3$)—CH$_2$C$_6$H$_5$ | H | H | H |
| 52 | — | 0 | 4-NH—C$_6$H$_{11}$ (cyclohexyl) | H | H | H |
| 53 | Cl | 4 | 4-NHCH(CH$_3$)$_2$ | H | H | H |

EXAMPLE 54

Following a procedure similar to that described in Example 1A but employing 3.1 g of 2-(1-ethyl-2-methyl-3-indolylcarbonyl)benzoic acid and 3.0 g of 4-dimethylamino-N-phenylaniline there was obtained 2.8 g of 3-(1-ethyl-2-methyl-3-indolyl)-3-[N-(4-dimethylamino)-phenyl-N-phenylamino]phthalide, m.p. 77°–90° C. A toluene solution of the product contacted with acidic clay or phenolic resin developed a brown-colored image.

EXAMPLE 55

Following a procedure similar to that described in Example 1A but employing 3.1 g of 2-(1-ethyl-2-methyl-3-indolylcarbonyl)benzoic acid and 2.3 g of methyl 2-anilinobenzoate there was obtained 0.4 g of 3-(1-ethyl-2-methyl-3-indolyl)-3-[N-(2-methoxycarbonylphenyl)-N-phenylamino]phthalide, m.p. 80°–115°. A toluene solution of the product contacted with acidic clay or phenolic resin developed a pink-colored image.

EXAMPLE 56

Following a procedure similar to that described in Example 1A but employing 3.1 g of 2-(1-ethyl-2-methyl-3-indolylcarbonyl)benzoic acid and 3.0 g of 4,4'-bis(-dimethylamino)diphenylamine there was obtained 1.8 g of 3-(1-ethyl-2-methyl-3-indolyl)-3-[N-(4-dimethylaminophenyl)-N-(4-dimethylamino)-phenylamino]phthalide, m.p. 76°–85° C. A toluene solution of the product contacted with acidic clay or phenolic resin developed a grape-colored image.

EXAMPLE 57

Following a procedure similar to that described in Example 1A but employing 4.5 g of 2-(1-ethyl-2-methyl-3-indolylcarbonyl)benzoic acid and 3.4 g of 4-acetamido-N-phenylaniline there was obtained 3.8 g of 3-(1-ethyl-2-methyl-3-indolyl)-3-[N-(4-acetamido-phenyl)-N-phenylamino]phthalide, m.p. 93°–116° C. A toluene solution of the product contacted with acidic clay or phenolic resin developed a yellow-colored image.

EXAMPLE 58

Following a procedure similar to that described in Example 1B but employing 3.1 g of 2-(1-ethyl-2-methyl-3-indolylcarbonyl)benzoic acid and 5.0 g of 4-octyl-4'-arylalkyldiphenylamine there was obtained 0.4 g of 3-(1-ethyl-2-methyl-3-indolyl)-3-[N-(4-octylphenyl)-N-(4-arylalkyl)phenylamino]phthalide, m.p. 105°–121° C. A toluene solution of the product contacted with acidic clay or phenolic resin developed a yellow-colored image.

EXAMPLE 59

Following a procedure similar to that described in Example 2B but employing 10.0 g of 2-(1-ethyl-2-methyl-3-indolylcarbonyl)benzoic acid and 13.0 g of 4,4'-dioctyldiphenylamine there was obtained a quantitative yield of 3-(1-ethyl-2-methyl-3-indolyl)-3-[N,N-bis-(4-octylphenyl)amino]phthalide, m.p. 106°108° C. A toluene solution of the product contacted with acidic clay or phenolic resin developed a yellow-colored image.

EXAMPLE 60

Following a procedure similar to that described in Example 1B but employing 2.6 g. of 4-(dimethylamino)-2-(1-ethyl-2-methyl-3-indolylcarbonyl)benzoic acid, 1.7 g. of diphenylamine and 5 ml. of acetic anhydride and stirring the reaction mixture 3 days at room temperature there was obtained 0.4 g. of 5-(dimethylamino)-3-(diphenylamino)-3-(1-ethyl-2-methyl-3-indolyl)phthalide, m.p. 192°–195° C. This product produced a yellow image on acidic clay and phenolic resin.

EXAMPLE 61

A solution containing 1.46 g. of the color former of Example 1B in 60 ml. of isopropylbiphenyl and a solution containing 5 g. of carboxymethylcellulose in 200 ml. of water were mixed and emulsified by rapid stirring. The desired particle size (5 microns) was checked by microsccope. To the emulsion was added a solution containing 15 g. of pigskin gelatin in 120 ml. of water. The pH was adjusted to 6.5 with 10% aqueous sodium hydroxide with rapid stirring, and following the gradual addition of 670 ml. of water at 50° C. the pH was adjusted to 4.5 with 10% aqueous acetic acid with continued rapid stirring. After 5 minutes the mixture was cooled to 15° C., treated with 10 g. of 25% aqueous glutaraldehyde and rapidly stirred for 15 minutes. The resulting microcapsule dispersion was stirred more slowly overnight, diluted with water to 1120 g. and coated on white typewriter paper sheets (0.0015 in. film thickness). The sheets were air dried. Duplicate typewritten images were made on receiving sheets coated with either phenolic resin or acidic clay. The color former of Example 1B produced a yellow colored image on both types of receiving sheets.

EXAMPLE 62

Following a procedure similar to that described in Example 45 but substituting soy oil for isopropylbiphenyl, the color former of Example 6 was microencapsulated and coated on a transfer sheet. The color former developed an orange colored image on both types of receiving sheets.

EXAMPLE 63

A polyvinyl alcohol dispersion of the color former of Example 7 was prepared by shaking 1 hour on a paint shaker a mixture containing 2.0 g. of the color former, 3.7 g. of water, 8.6 g. of 10% aqueous polyvinyl alcohol and 10 g. of zirconium grinding beads. A polyvinyl alcohol dispersion of bisphenol A was prepared by shaking a mixture containing 9.8 g. of bisphenol A, 18.2 g. of water, 42 g. of 10% aqueous polyvinyl alcohol and 70 ml. of zirconium grinding beads. The coating mixture was made by combining and thoroughly mixing 2.1 g. of the polyvinyl alcohol dispersion of the color former with 47.9 g. of the polyvinyl alcohol dispersion of bisphenol A. The coating mixture was applied (at thicknesses of 0.003 in. and 0.0015 in.) to white mimeo paper sheets and the sheets were dried at room temperature. Contacting the coated sheets with a heated stylus at a temperature between 110° C. and 150° C. produced a dark orange image.

We claim:

1. In a pressure-sensitive carbonless duplicating system or thermal marking system, a support sheet coated on one side with a color-forming substance comprising a compound having the formula

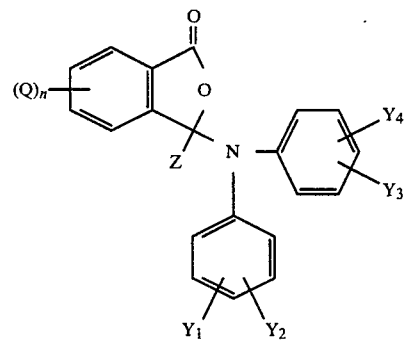

wherein:

Q is selected from the group consisting of di-lower-alkylamino, nitro, halo and COX where X is hydroxyl, benzyloxy, alkoxy having from 1 to 18 carbon atoms or OM where M is an alkali metal cation, an ammonium cation or a mono-, di- or trialkylammonium cation having from 1 to 18 carbon atoms;

n is 0; or 1 when Q is di-lower-alkylamino, nitro or COX; or from 1 to 4 when Q is halo;

$Y_1$, $Y_2$, $Y_3$ and $Y_4$ are the same or different and are selected from the group consisting of hydrogen, halo, hydroxyl, lower-alkoxy, alkyl having from 1 to 9 carbon atoms, phenyl-lower-alkyl, $COOR_4$ and $NR_5R_6$ where $R_4$ and $R_5$ are hydrogen or lower-alkyl and $R_6$ is hydrogen, lower-alkyl, cycloalkyl having from 5 to 7 carbon atoms, or lower alkanoyl;

Z is selected from the group consisting of

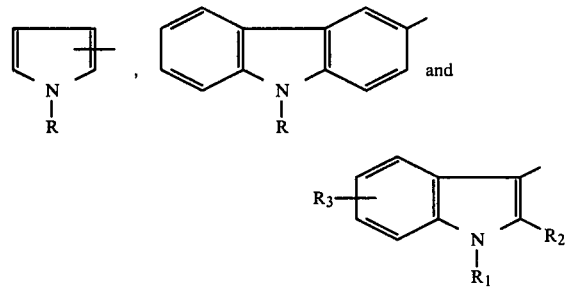

in which:

R is hydrogen or non-tertiary alkyl having from 1 to 4 carbon atoms;

$R_1$ is hydrogen, or non-tertiary alkyl having from 1 to 18 carbon atoms;

$R_2$ is hydrogen, phenyl or non-tertiary alkyl having from 1 to 4 carbon atoms; and $R_3$ is hydrogen, non-tertiary alkyl having from 1 to 4 carbon atoms or non-tertiary alkoxy having from 1 to 4 carbon atoms.

2. In a pressure-sensitive carbonless duplicating system or thermal marking system, a support sheet according to claim 1 wherein Z is a radical having the formula

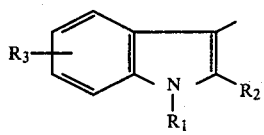

in which:
R₁ is hydrogen or non-tertiary alkyl having from 1 to 18 carbon atoms;
R₂ is hydrogen, phenyl or non-tertiary alkyl having from 1 to 4 carbon atoms; and
R₃ is hydrogen, non-tertiary alkyl having from 1 to 4 carbon atoms or non-tertiary alkoxy having from 1 to 4 carbon atoms.

3. In a pressure-sensitive carbonless duplicating system or thermal marking system, a support sheet according to claim 2 wherein R₃, Y₁ and Y₃ are each hydrogen and Y₂ and Y₄ are the same or different and are selected from the group consisting of hydrogen, lower-alkoxy, alkyl having from 1 to 9 carbon atoms and NR₅R₆ where R₅ and R₆ are each lower-alkyl.

4. In a pressure-sensitive carbonless duplicating system or thermal marking system, a support sheet according to claim 3 wherein n is 0.

5. In a pressure-sensitive carbonless duplicating system, a support sheet according to claim 4 coated on one side with a layer of pressure-rupturable microcapsules containing a liquid solution of the color-forming substance.

6. A thermal marking system according to claim 4 comprising a support sheet coated on one side with a layer containing a mixture of the color-forming substance and an acidic developer arranged such that application of heat will produce a mark-forming reaction between the color-forming substance and the acidic developer.

7. In a pressure-sensitive carbonless duplicating system or thermal marking system, a support sheet according to claim 3 wherein Q is halo and n is 1 to 4.

8. In a pressure-sensitive carbonless duplicating system, a support sheet according to claim 6 coated on one side with a layer of pressure-rupturable microcapsules containing a liquid solution of the color-forming substance.

9. A thermal marking system according to claim 7 comprising a support sheet coated on one side with a layer containing a mixture of the color-forming substance and an acidic developer arranged such that application of heat will produce a mark-forming reaction between the color-forming substance and the acidic developer.

10. In a pressure-sensitive carbonless duplicating system or thermal marking system, a support sheet according to claim 3 wherein n is 1 and Q is COX and X is benzyloxy or alkoxy having from 1 to 18 carbon atoms.

11. In a pressure-sensitive carbonless duplicating system, a support sheet according to claim 8 coated on one side with a layer of pressure-rupturable microcapsules containing a liquid solution of the color-forming substance.

12. A thermal marking system according to claim 8 comprising a support sheet coated on one side with a layer containing a mixture of the color-forming substance and an acidic developer arranged such that application of heat will produce a mark-forming reaction between the color-forming substance and the acidic developer.

13. In a hectographic copying system, a support sheet coated on one side with a layer containing a color-forming substance comprising a compound having the formula

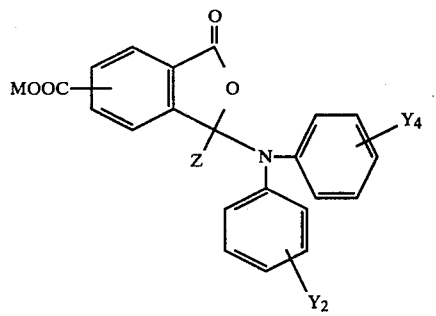

wherein:
M is an alkali metal cation, an ammonium cation or a mono-, di- or tri-alkylammonium cation having from 1 to 18 carbon atoms;
Y₂ and Y₄ are the same or different and are selected from the group consisting of hydrogen, lower-alkoxy, alkyl having from 1 to 9 carbon atoms, and NR₅R₆ where R₅ and R₆ are each lower-alkyl; and
Z is a radical having the formula

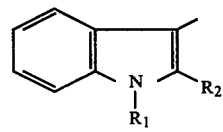

in which R₁ is hydrogen or non-tertiary alkyl having from 1 to 18 carbon atoms, and
R₂ is hydrogen, phenyl or non-tertiary alkyl having from 1 to 4 carbon atoms.

* * * * *